(12) United States Patent
Hionakis (10) Patent No.: US 10,117,523 B1
(45) Date of Patent: Nov. 6, 2018

(54) INFANT SWING

(71) Applicant: Anna Hionakis, LaPlace, LA (US)

(72) Inventor: Anna Hionakis, LaPlace, LA (US)

( * ) Notice: Subject to any disclaimer, the term of this patent is extended or adjusted under 35 U.S.C. 154(b) by 0 days.

(21) Appl. No.: 15/619,540

(22) Filed: Jun. 12, 2017

(51) Int. Cl.
| | |
|---|---|
| *A63G 9/16* | (2006.01) |
| *A47D 9/04* | (2006.01) |
| *A47D 15/00* | (2006.01) |
| *A47D 13/02* | (2006.01) |
| *A61M 21/02* | (2006.01) |
| *A47F 8/00* | (2006.01) |
| *A47D 9/00* | (2006.01) |
| *A61M 21/00* | (2006.01) |

(52) U.S. Cl.
CPC ............... *A47D 9/04* (2013.01); *A47D 13/02* (2013.01); *A47D 15/008* (2013.01); *A47F 8/00* (2013.01); *A61M 21/02* (2013.01); *A61M 2021/005* (2013.01); *A61M 2021/0022* (2013.01); *A61M 2021/0027* (2013.01); *A61M 2240/00* (2013.01)

(58) Field of Classification Search
CPC ... A63G 9/00; A63G 9/12; A63G 9/16; A47D 9/00; A47D 9/02; A47D 9/04
USPC ............. 472/118–119; 446/330, 331, 71–72; 5/108, 109
See application file for complete search history.

(56) References Cited

U.S. PATENT DOCUMENTS

| | | | |
|---|---|---|---|
| 2,637,936 A | 5/1953 | Dale | |
| 3,605,305 A | 9/1971 | Grigorian | |
| 5,470,270 A | 11/1995 | Beamon | |
| 5,941,599 A * | 8/1999 | Roberts | A47C 3/16 297/115 |
| 6,019,659 A * | 2/2000 | Walters | A61F 7/007 219/200 |
| 6,692,330 B1 * | 2/2004 | Kulick | A63H 3/28 434/308 |
| 6,939,194 B2 | 9/2005 | Bapst | |
| 6,966,082 B2 | 11/2005 | Bloemer | |
| 7,845,728 B2 * | 12/2010 | Chen | A47D 13/10 297/260.1 |
| 8,776,285 B2 * | 7/2014 | Shane | A47D 9/02 5/105 |
| 2004/0077287 A1 * | 4/2004 | Odiwo | A47D 9/04 446/491 |
| 2006/0130220 A1 | 6/2006 | Morgan | |
| 2007/0224909 A1 | 9/2007 | Schoenfelder | |

* cited by examiner

*Primary Examiner* — Kien Nguyen
(74) *Attorney, Agent, or Firm* — Norton IP Law Firm; Taylor M. Norton (57) ABSTRACT

The present disclosure provides for an infant swing simulating a human form preferably comprising an animated body including an upper body portion simulating a human trunk, arms, shoulders, neck and head portions as well as a lower body portion. A frontally worn infant carrier is preferably connected to the shoulders and waist of the animated body. The lower body portion is operatively connected to a base having a motor to pivot the body in an oscillatory manner. The head portion preferably includes a 3D-printed interchangeable face mask resembling a caretaker of the infant. In a preferred embodiment, the animated body includes a sound recorder, speaker, vibrating motor, and heating elements disposed therein for soothing and comforting an infant.

33 Claims, 7 Drawing Sheets

INFANT SWING

BACKGROUND OF THE INVENTION

Field of the Invention

The present invention generally relates to improvements in baby cradles and more particularly relates to baby infant swing devices for caretakers and infants which will substantially increase the soothing aspects of infant swings thereby alleviating the musculoskeletal systems and fatigue of the bodies of caretakers.

Description of the Related Art

People in many different cultures around the world often enjoy taking care of infants, and it is well known that agitated infants exhibit their discomfort or frustration by crying out, seeking to be calmed and soothed by a parent or other caretaker. Many types of baby cradles, rockers, and swings have been proposed to soothe and comfort infants through automatic rocking, bouncing or swinging of infants, attempting to alleviate the need for such activity in the arms of a parent or other caretaker.

Various different types of infant cradles and swings are well known. Conventional infant rocking chairs can only produce either only a back-and-forth motion or an up-and-down motion. However, a curved swinging motion along a horizontal arc in which a back-and-forth motion, so as to simulate the motion usually made by a person taking care of and holding an infant in his or her arms, would be able to impart greater comfort to the infant. Furthermore, conventional driving devices for driving infant rocking chairs include interconnected gears, which generate a large amount of unpleasant noises during operation and those noises are conventionally located directly adjacent to the infant's head, which can be unsettling for the infant.

Everyday, infants are held and cared for and are often placed in a swing or in a cradle. For instance, while in one's home, parents, guardians or caretakers may need to hold and swing an infant to calm down and soothe a crying child, so that the infant can rest and sleep better. When a person needs to take a break from holding up and supporting the weight of the infant, he or she may often look for a couch, bed or swing to place the infant. At times, such placement is not acceptable to the child who wants to be held upright and comforted. Therefore, many adults are left uncomfortably holding an infant for prolonged periods of time without any rest of the adult's arms, back or legs, or alternatively, the infant is left to cry-out while uncomfortably and unsoothingly left in a lonesome environment. Therefore, most people would like to provide to the infant their familiar voices and sounds so as to help calm and sooth the child.

U.S. Pat. No. 6,966,082 issued on Nov. 22, 2005 to Bloemer et al. discloses a complicated apparatus aimed at pure vertical motion having scissor mechanisms and springs for reciprocating an infant in an vertically upward and downward movement.

U.S. Pat. No. 7,845,728 issued on Dec. 7, 2010 to Chen et al. discloses a complicated assembly having a driving device for driving a seat body of an infant rocking chair supported by axles and parallel rows of rollers along several guide tracks to move it linearly forward and backward in a reciprocating manner as well as to move it vertically upward and downward, attempting to provide comfort for an infant.

While these units may be suitable for the particular purpose employed, they would not be as suitable for the purposes of the present invention as disclosed hereafter.

Each patent application identified above is incorporated herein by reference in its entirety.

Accordingly, there is a need for a compact portable lightweight and strong infant swing apparatus for securely supporting and soothing an infant without complex assembly and set up.

A need exists for an infant swing which allows for easy adjustment of the height of the infant swing while the swing stands in an upright freestanding position.

One object of the present invention is to provide a mannequin infant swing resembling a parental person operatively configured with sound, warmth, vibratory, and voice generators, operatively embedded within a body and arms so that when the infant needs soothing, the infant swing provides a human simulating swinging movement thereof.

Another object of the present invention is to provide a mannequin infant swing including a voice recorder for soothing a crying infant, wherein the rotating figure movements of and sounds emitted by the mannequin swing are capable of attracting the attention of a young child to listen to the voice message.

As disclosed in this application, the inventor has discovered novel and unique devices and methods for soothing and tending to an infant, which exhibit superlative properties without being dependent on complex and expensive components.

Embodiments of the present invention provide for infant swings and methods as defined in the detailed description and annexed claims which provide for improved swinging and nurturing characteristics in order to efficiently swing and soothe infants.

SUMMARY OF THE INVENTION

It is one prospect of the present invention to provide an infant swing that simulates the animated body and appearance of a caretaker. It is a further an object of the present invention to provide a soft-sided infant carrier which is capable of simulating a front carrier configured upon a body of a human caretaker while the infant remains safely and securely seated in the carrier. It is another object of the present invention to provide a soft-sided infant swing which is capable of conveniently assuming various carrying and swinging positions.

It yet another prospect of the present invention to provide an infant swing of simple but effective construction which can be used with various size infants, to provide a curved swinging motion along a horizontal arc in which a back-and-forth motion so as to simulate the motion usually made by a person taking care of and holding an infant in his or her arms.

It is yet another aim of the present invention to provide an improved infant swing that provides soothing sounds familiar to the infant, that provides soothing warmth and vibration for an infant, and that helps to prevent flat head syndrome.

Additional objects, advantages and novel features of this invention shall be set forth in the description that follows, and in part will become apparent to those skilled in the art upon examination of the following specification of my be learned by the practice of the invention. The objects and advantages of the invention may be realized and attained by means of the instrumentalities, combinations, and devices particularly pointed out in the appended claims.

The following presents a simplified summary of the present disclosure in a simplified form as a prelude to the more detailed description that is presented herein.

Therefore, to achieve the foregoing and other objects and in accordance with the purposes and embodiments of the present invention, as embodied and described herein, there is provided an infant swing directed to an animated body having a flexible hollow casing simulating a human body form. The animated body has an upper body portion forming a simulated human trunk, arms, shoulders, neck and head portions of a human being, and it also has a lower body portion. The arms are preferably sized and configured to firmly and removably engage and secure a portion of a body of the infant, such that the arms simulate the arms of a caregiver. The infant swing includes a frontally worn infant carrier which is preferably made of a flexible fabric and is configured to receive and hold an infant. The infant carrier portion preferably has shoulder straps that are removably connected to the shoulders of the animated body of the infant swing, such that reciprocating motion of the animated body imparts swinging motion to the infant carrier along a horizontal arc relative to a vertical pivot axis of the animated body. The infant carrier portion preferably includes a base containing a motor which has a vertically extending shaft, which is coaxial alignment with the vertical pivot axis of the animated body, such that the shaft is operatively connected to the lower body portion of the animated body for pivoting the animated body in a reciprocating motion relative to the base, and thus, swinging the infant relative to the animated body for comforting the infant.

In a preferred embodiment, the head portion includes an interchangeable face portion resemblant of a face of a caretaker to comfort the infant. The interchangeable face portion is preferably customized to resemble a face of a person familiar to the infant, wherein the face portion is 3D-printed mask removably connected to the head portion of the infant swing. The animated body of the infant swing also preferably includes a sound/voice recorder that is disposed within the animated body, preferably within the head of the animated body and configured to record or store a sound, such as a voice or particular music, from a user to form a voice message or song to be played for the infant.

In another embodiment, the arms have one or more vibrating motors configured to soothe the infant, such that the arms can be rotated about the trunk of the animated body and positioned to engage the infant at varying locations of the infant's body, to provide soothing vibration to the infant, at the option of the user.

In yet another preferred embodiment of the present invention, there is provided a mannequin infant swing having a mannequin torso which includes an upper chest portion and a lower abdominal portion. The mannequin infant swing preferably has an infant carrier having straps configured to be operatively worn by the mannequin torso. The straps can hang from the mannequin torso in a manner resemblant of a caretaker. The infant carrier is preferably fabricated and configured as a flexible fabric adapted to receive and securely hold an infant along the frontal surface of the upright mannequin torso. The mannequin infant swing preferably includes a head portion that is operatively connected to the mannequin torso by a neck portion, resemblant of a caretaker. The mannequin infant swing also preferably has a base containing a motor, and the motor has a vertical motor shaft extending upward from the base and configured to pivotally oscillate the vertical shaft relative to the base. Preferably, the vertical shaft is connected to the lower abdominal portion such that, in operation, pivoting of the vertical shaft imparts swinging of said infant carrier relative to the mannequin torso.

In embodiments of the present invention, a infant does not ride side to side on the tracks of a machine like in current infant swing devices, but instead the infant is allowed to rotate and swing along a horizontal arc, closely mimicking the movement of a caretaker rocking an infant in the caretaker's arms. In some embodiments, swinging along a horizontal arc means reciprocating back and forth in a direction along an arc within a plane which is perpendicular to and surrounds the vertical axis of the infant swing, and reciprocating such infant in a direction oriented through the median or sagittal plane. In yet other embodiments, swinging along a horizontal arc means reciprocating back and forth in a direction along an arc within a plane which is perpendicular to and surrounds the vertical axis of the infant swing, and reciprocating such infant in a direction oriented through the infant's axial plane.

These and other features, aspects, and advantages of the present invention will become better understood with reference to the following description and appended claims.

BRIEF DESCRIPTION OF THE DRAWINGS

Illustrative embodiments of the present invention are described herein with reference to the accompanying drawings, in which.

DETAILED DESCRIPTION

For a further understanding of the nature and function of the embodiments, reference should be made to the following detailed description. Detailed descriptions of the embodiments are provided herein, as well as, the best mode of carrying out and employing the present invention. It will be readily appreciated that the embodiments are well adapted to carry out and obtain the ends and features mentioned as well as those inherent herein. It is to be understood, however, that the present invention may be embodied in various forms. Therefore, persons of ordinary skill in the art will realize that the following disclosure is illustrative only and not in any way limiting, as the specific details disclosed herein provide a basis for the claims and a representative basis for teaching to employ the present invention in virtually any appropriately detailed system, structure or manner. It should be understood that the devices, materials, methods, procedures, and techniques described herein are presently representative of various embodiments. Other embodiments of the disclosure will readily suggest themselves to such skilled persons having the benefit of this disclosure.

For purposes of clarity and orientation with respect to a person, referred to herein as a user, it is noted that a transverse (also known as axial or horizontal) plane is an X-Z plane, parallel to the ground. A frontal (also known as coronal) plane is a Y-X plane, perpendicular to the ground, which (in humans) separates the anterior from the posterior, the front from the back, the ventral from the dorsal. A sagittal (also known as lateral) plane is an Y-Z plane, perpendicular to the ground, which separates left from right. Objects are coplanar if they all lie in the same plane. For example, one axis is coplanar with another axis when the two axes lie in the same plane.

As used herein, "axis" means a real or imaginary straight line about which a three-dimensional body is symmetrical. A "vertical axis" means an axis perpendicular to the ground (or put another way, an axis extending upwardly and downwardly). A "horizontal axis" means an axis parallel to the ground.

Figure 1:
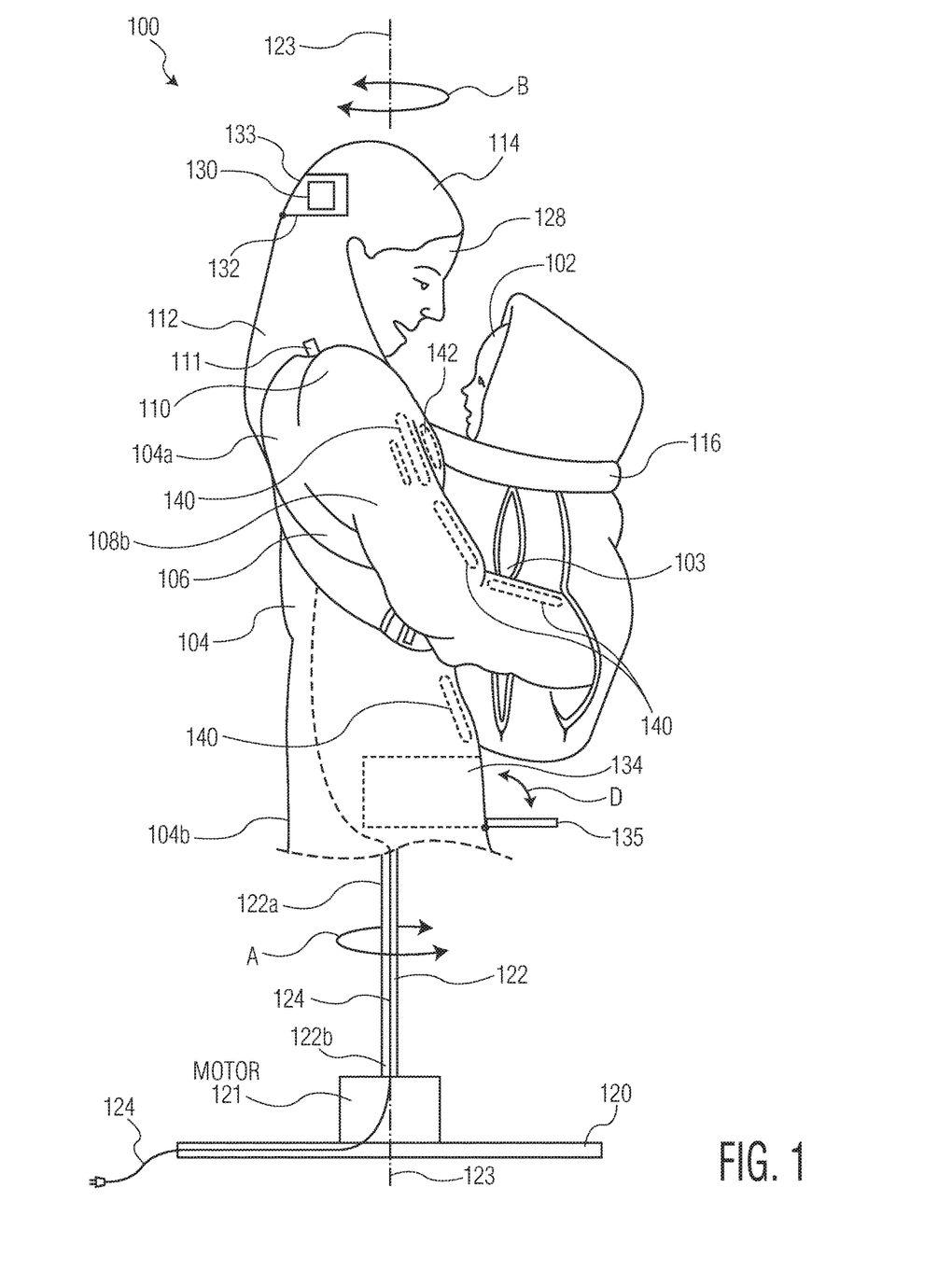
FIG. 1 is a side elevation view of an exemplary infant swing.
Figure 2:
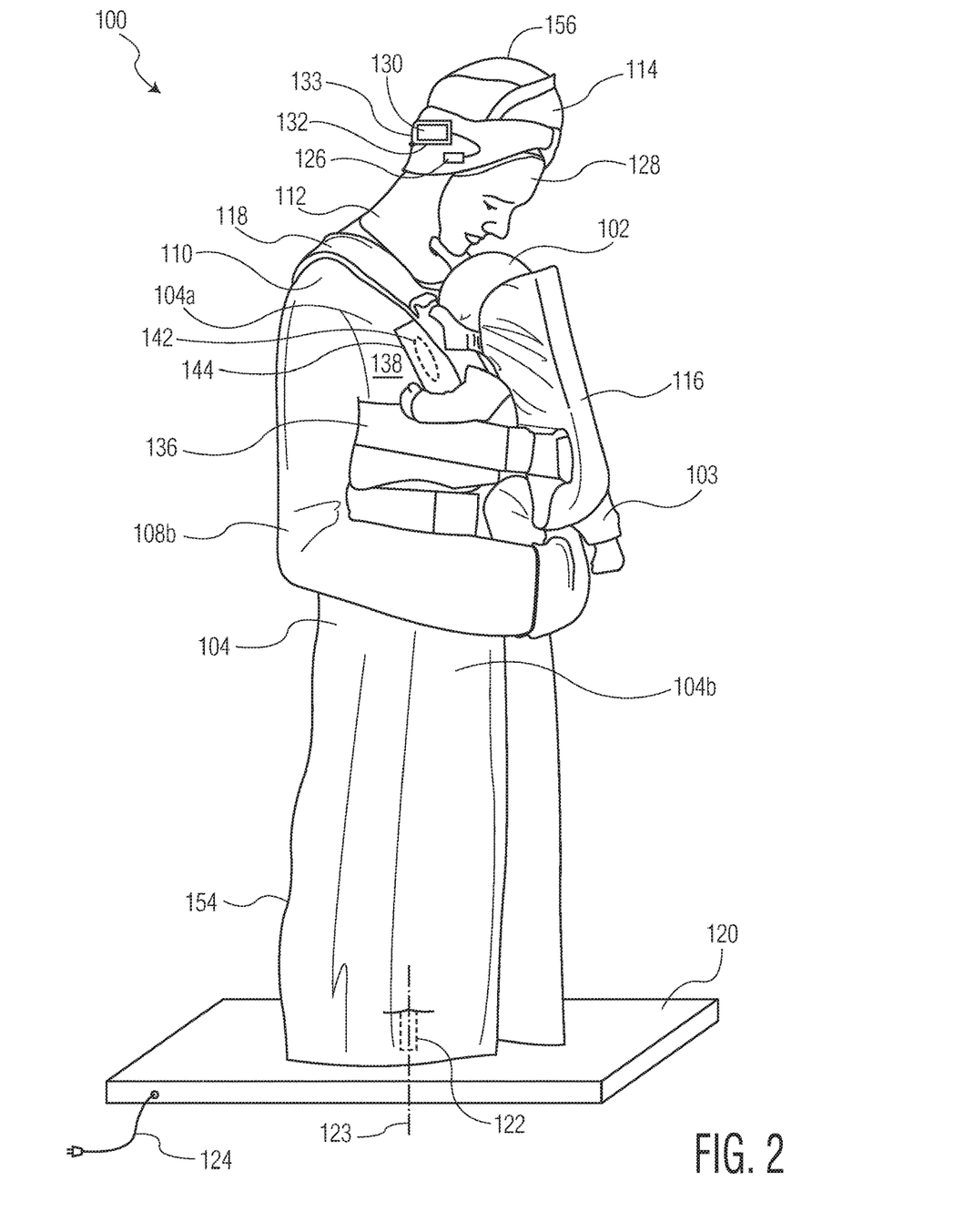
FIG. 2 is a perspective view of an exemplary infant swing according to another embodiment of the present invention.

Referring initially to FIGS. 1-2, the basic constructional details and principles of operation of one embodiment of an infant swing 100 for receiving and supporting an infant 102 according to a preferred embodiment of the present invention will be discussed.

In FIGS. 1-2, an infant swing 100 according to a preferred embodiment of the present invention is provided. As illustrated in FIG. 1, the infant swing 100 comprises an animated body 104 comprising a flexible hollow casing simulating a human form. The animated body 104 includes an upper body portion 104a forming a simulated human trunk 106, arms 108, shoulders 110, neck 112 and head 114 portions. The animated body 104 also includes a lower body portion 104b opposite the upper body portion 104a.

The arm portions 108 are preferably sized and configured contralateral to each other, meaning, in a preferred embodiment, one arm 108 is disposed on each side of the trunk 106 of the animated body 104. For example, the left arm 108a is preferably contralateral to the right arm 108b of the animated body 104. In a preferred embodiment, each arm 108 is operatively connected to a shoulder 110 of the animated body 104 and is adapted to firmly and removably engage and secure a portion of an infant's body 103, as illustrated in the embodiments in FIGS. 1-2.

Referring to FIGS. 1-2, the animated body 104 further comprises a frontally hung or worn infant carrier 116, which is preferably constructed of a flexible fabric and is configured to receive an infant 102. The infant carrier 116 has shoulder straps 118 that are removably attached to the shoulders 110 of the trunk 106 of the animated body 104 such that reciprocating motion (arrow A) of the animated body 104 imparts swinging motion (arrow B) to the infant carrier 116. In a preferred embodiment, the shoulders 110 have hooks 111 disposed atop each respective shoulder 110, and the shoulder straps 118 connect to the hooks 111 as illustrated in FIG. 1.

The animated body 104 further comprises a preferably wide base 120 that has an electric motor 121 disposed within the base 120, and the motor 121 has a vertically extending shaft 122 which is operatively connected to the bottom of the lower body portion 104b of the animated body 104 for pivoting the animated body 104 in a reciprocating motion above and relative to the base 120 as illustrated by arrow A, and thus, resulting in swinging the infant carrier 116 and infant 102 along a horizontal arc (arrow B) relative to a vertical axis 123 of the vertical shaft 122 that is connected to the animated body 104 for comforting the infant 102. The arc arrow B in FIG. 1 illustrates that the infant 102 within the infant carrier 116 tangentially moves along arc B as a result of pivoting forces illustrated by arrow A imparted by the motor 121. Embodiments of the present invention have improved emulation of actual swinging and soothing of a caretaker person and exhibit improvements over previous swinging devices because the true pivot point 123 for turning is established around which the frontally hung or worn carrier 116 horizontally oscillates, enabling an infant 102 to horizontally oscillate back and forth in conjunction with the pivoting animated body 104.

The motor 121 preferably comprises an electric motor, or alternatively comprises a spring-wound mechanism (not shown). The motor 121 is preferably configured as a variable speed motor 121. The motor 121 is preferably operated or controlled by a remote control such as a smartphone, such as, for example an iPhone. In a preferred embodiment, the vertical shaft 122 is rotated directly from a low-speed, high-torque motor 121, without a gearbox. In an alternative embodiment, a relatively high-speed, low torque motor 121 is used with a reduction gearbox (not shown), whereby the motor 121 output is converted to a low-speed, high-torque output from the gearbox.

The motor 121 shown in the Figures is electrically connected to a power supply, such as a DC power supply or an AC outlet, by a power cord or electrical wire 124. Alternatively, the motor 121 may be electrically connected to a battery 126. In another embodiment, the infant swing 100 is configured such that the motor 121 may be electrically connected to an accessory power outlet of an automobile, such as a cigarette lighter socket.

In yet another embodiment, the vertical support shaft 122 is provided comprising an upper portion 122a and a lower portion 122b, and the lower portion 122b forms a socket that is configured to telescopically receive and closely surround the upper portion 122a of the vertical shaft 122, enabling simple and efficient adjustment of the height of the animated body 104 at the option of the user.

The head portion 114 of the infant swing 100 preferably comprises an interchangeable simulated human face portion 128 resemblant of a face of a user, preferably of a caretaker, adapted to comfort the infant 102 by emulating a familiar face for the infant 102. The face portion 128 is preferably positioned in close proximity to the infant 102, and the infant 102 is preferably held in an upright position by the infant carrier 116, as illustrated in FIGS. 1-2, thereby closely assimilating being held by real life caretaker person. In another embodiment, the head portion 114 has attached to it an interchangeable simulated animal face portion (128 is an exemplary simulated human face portion) resemblant of a face of an animal configured to comfort the infant 102.

Figure 5:
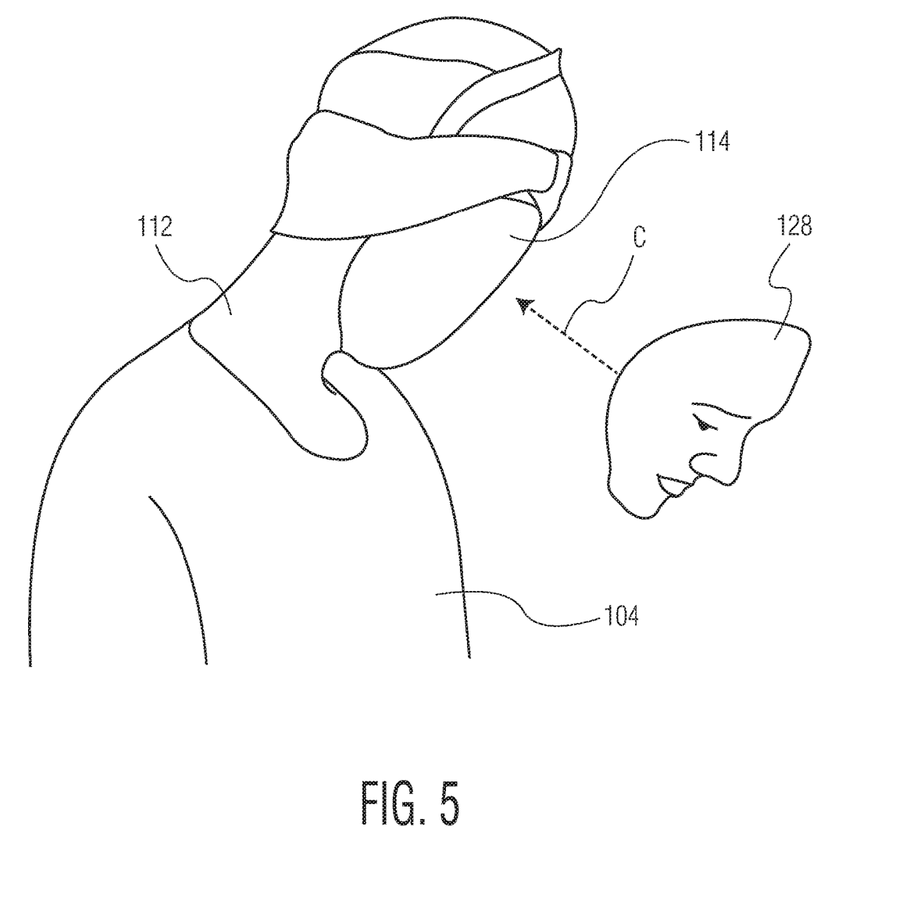
FIG. 5 is a close-up view of an embodiment showing an exemplary interchangeable face in a disjoined position.

In a preferred embodiment, the face portion 128 is preferably 3D printed and configured to detachably connect to the front of the head portion 114 of the infant swing 100, as illustrated by arrow C in FIG. 5.

In yet another preferred embodiment, the infant swing 100 further comprises a sound/voice recorder and converter 130, preferably disposed within the head portion 114 of the animated body 104. The sound recorder and converter 130 is electronically connected to a power source 126 such as a battery as illustrated in FIG. 2. The sound/voice recorder and converter 130 may be configured as a voice recorder that is adapted to record a voice from a user to form a voice message. The sound/voice recorder and converter 130 is preferably disposed within the head portion 114 of the animated body 104 and converts the voice messages into an audible form to soothe the infant 102, by preferably playing a voice messages sounding of a voice familiar to the infant 102. In an alternative embodiment, (not shown) the sound recorder and converter 130 is configured within the left arm 108a, right arm 108b, or within both the left arm 108a and right arm 108b of the animated body 104 of the infant swing 100. Such embodiments enable directional positioning and focusing of the sound playing therefrom, at the option of the user.

FIG. 1 illustrates an exemplary preferred location of the sound recorder and converter 130 that is positioned within a cavity 132 formed by the head portion 114 of the animated body 104. In a preferred embodiment, the head portion 114 of the animated body 104 is configured to receive and contain the voice/sound recorder and converter 130. Preferably, the head portion 114 has a hinged door 133 providing access to the sound/voice recorder and converter 130 by movement between open and closed positions relative to the head cavity 132. At the option of the user, the sound recorder and converter 130 can be removed from the head portion 114 and configured with various sounds desired by the user.

In a preferred embodiment, the sound recorder and converter 130 is configured to connect to a smartphone, such as an iPhone, by a wire, such that sound/audio files can be transferred from the smartphone to the sound recorder and converter 130.

In one embodiment, the infant swing 100 comprises a sound recorder and converter 130 adapted to record a heartbeat sound. The sound recorder and converter 130 is preferably disposed within the head portion 114 of the animated body 104, and in such embodiment, the sound converter is electrically connected with the sound recorder for converting the heartbeat sound into an audible form to provide a soothing heartbeat sound for the infant 102.

In another embodiment, the infant swing 100 further comprises a sound recorder disposed within the animated body 104, and the sound recorder is electronically connected to a power source and adapted to store music. In such embodiment, the sound converter is preferably disposed within the animated body 104 and is electrically connected to the sound recorder for converting said stored music, such as a lullaby, into an audible form for the infant. In another embodiment, the sound recorder 130 is adapted to record a womb sound, such that the sound converter 130 converts the womb sound into an audible form to be heard by the infant 102 while the infant 102 is closely held against the animated body 104. Due to the soothing sounds of a mother figure, it is often observed that infants rest more easily and effectively when hearing comforting sounds while rocking or swinging.

In yet another embodiment, one arm 108 of the animated body 104 comprises a vibrating motor 140 embedded within the arm 108 for soothing the infant when the arm 108 touches a portion of an outer surface of the body 103 of the infant 102, as illustrated in FIG. 1. In a preferred embodiment, the animated body 104 has two arms 108 and each arm 108 has a plurality of vibrating motors 140 embedded within the arm 108, as seen in FIG. 1. In other words, in embodiments of the present disclosure, the arms 108 are rotatable and positionable by a user so as to engage an infant's body 102 and thus provide soothing vibration to the infant 102 at varying locations of the infant's body 102, at the option of the user.

In yet another embodiment, the simulated human trunk 106 comprises at least one vibrating motor 142 embedded within the simulated human trunk 106 for soothing the infant 102 when the infant 102 is positioned within the frontally worn infant carrier 116 and preferably held in an upright position by the infant carrier 116, as illustrated in FIGS. 1-2.

The human trunk preferably comprises a vibrating motor 142 disposed in the upper body portion 104a and another vibrating motor 142 disposed within the lower body portion 104b of the animated body 104.

Preferably, the infant swing 100 can be controlled by a personal data assistant, such as for example, a smartphone.

In yet another preferred embodiment, each shoulder 110 of the infant swing 100 has a hook 111 extending atop the shoulder 110, such that shoulder straps 118 of the frontally worn infant carrier 116 are configured to hook thereupon and hang downwardly therefrom.

In yet another preferred embodiment of the infant swing 100, the lower body portion 104b of the animated body 104 defines a cavity 134 adapted for storage of the infant carrier 116 within such inner cavity 134. The lower body portion 104b preferably has a hinged door 135 providing access to such inner cavity 134 by movement between open and closed positions (exemplified by arrow D) relative to the cavity 134 and surface of the animated body 104. The frontally hung infant carrier 116 can be removed from the animated body 104 and stored within the inner cavity 134 of the animated body 104, at the option of the user.

Referring to FIG. 2, in yet another preferred embodiment of the present invention, a mannequin infant swing 100 is provided comprising a mannequin torso 104 having an upper chest portion 104a and a lower abdominal portion 104b. The lower abdominal portion 104b preferably has an abdominal cavity 134 formed therein for storage. The mannequin infant swing 100 comprises an infant carrier 116 comprising straps 118 operatively worn by the mannequin torso 104 as illustrated in FIG. 2. The infant carrier 116 is preferably constructed of a flexible fabric configured to receive and securely hold an infant 102 in an upright position. As can be seen, embodiments of the present invention help to prevent flat head syndrome in infants. The mannequin infant swing 100 comprises a head portion 114 operatively connected to the mannequin torso 104 by a neck portion 112. The head portion 114 is configured to receive a simulated human face mask 128, as seen in FIGS. 2-5.

As exemplified in FIG. 2, the mannequin infant swing 100 preferably has a wide base 120 having a motor 121 (not shown) preferably disposed within the base 120, and the motor 121 has a vertical motor shaft 122 extending upward therefrom. The motor 121 is configured to pivotally oscillate the vertical shaft 122 relative to the base 120, and the vertical shaft 122 is connected to the lower abdominal portion 104b of the mannequin torso 124 such that, in operation, pivoting of the vertical shaft 122 imparts swinging of the infant carrier 116 relative to the mannequin torso 104.

In one embodiment, the vertical shaft 122 is a telescoping shaft comprising an upper shaft portion 122a which is configured to extend into the lower shaft portion 122b in order to adjust the height of the mannequin torso 104.

Preferably, the mannequin infant swing 100 comprises a simulated human face mask 128 configured to reflect a face of a caretaker, and the simulated face mask 128 is a 3D-printed face mask. In yet another preferred embodiment, the mannequin infant swing 100 comprises a head portion 114 configured to receive a simulated animal face mask (not shown). The mannequin infant swing 100 preferably comprises a simulated animal face mask configured to reflect a face of an animal, wherein the face of the animal is appealing to the infant 102.

The mannequin infant swing 100 preferably has a voice recorder 130 disposed within a cavity 132 within the head portion 114, and the voice recorder 130 is electronically connected to a power source and adapted to record a voice from a user in order to form a voice message. A sound converter 130 is preferably disposed within the cavity 132 within the head portion 114, and the sound converter 130 is electrically connected with said voice recorder 130 for converting a voice message into an audible form for the infant to hear.

In yet another embodiment, the mannequin infant swing 100 comprises a sound recorder 130 disposed within the mannequin torso 104, and the sound recorder 130 is electronically connected to a power source and adapted to record a heartbeat sound. The sound converter 130 is preferably disposed within the mannequin torso 104, and the sound converter 130 is electrically connected with the sound recorder 130 for converting the heartbeat sound into an audible form, which preferably plays soothing heartbeat-simulating sounds in close proximity to the infant's head, since the infant 102 is preferably held in an upright position close to the mannequin torso 104, as exemplified in FIG. 2.

Referring to FIG. 2, in a preferred embodiment, the straps 118 of the infant carrier 116 comprise a set of shoulder straps 118 and a set of side straps 136 configured to extend around the mannequin torso 104, from which is suspended an infant holder 116 into which the infant 102 is placed and supported.

Preferably, the upper chest portion 104a of the mannequin infant swing 100 comprises an anterior wall 138 having a heating pad 144 electrically connected to a power source for providing warmth to the infant 102 when positioned close to the upper chest portion 104a and held within the infant carrier 116.

In another embodiment, the upper chest portion 104a of the mannequin infant swing 100 has an anterior wall 138 having a vibrating motor 142 disposed within the chest portion 104a and electrically connected to a power source, to provide soothing vibrating sensation to an infant 102 while held within the infant carrier 116 in an upright position, and held against the chest portion 104a, as illustrated in FIG. 2.

In yet another embodiment, the mannequin infant swing 100 comprises one or more arms 108 operatively connected to the mannequin torso 104, wherein at least one arm 108 comprises a vibrating motor 140 disposed therein electrically connected to a power source.

Preferably, the anterior surface 138 of the lower abdominal portion 104b has a hinged lid 135 providing access to a cavity 134 defined by the lower abdominal portion 104b, which is adapted for storage of the infant carrier 116 within the cavity 134.

Figure 3A:
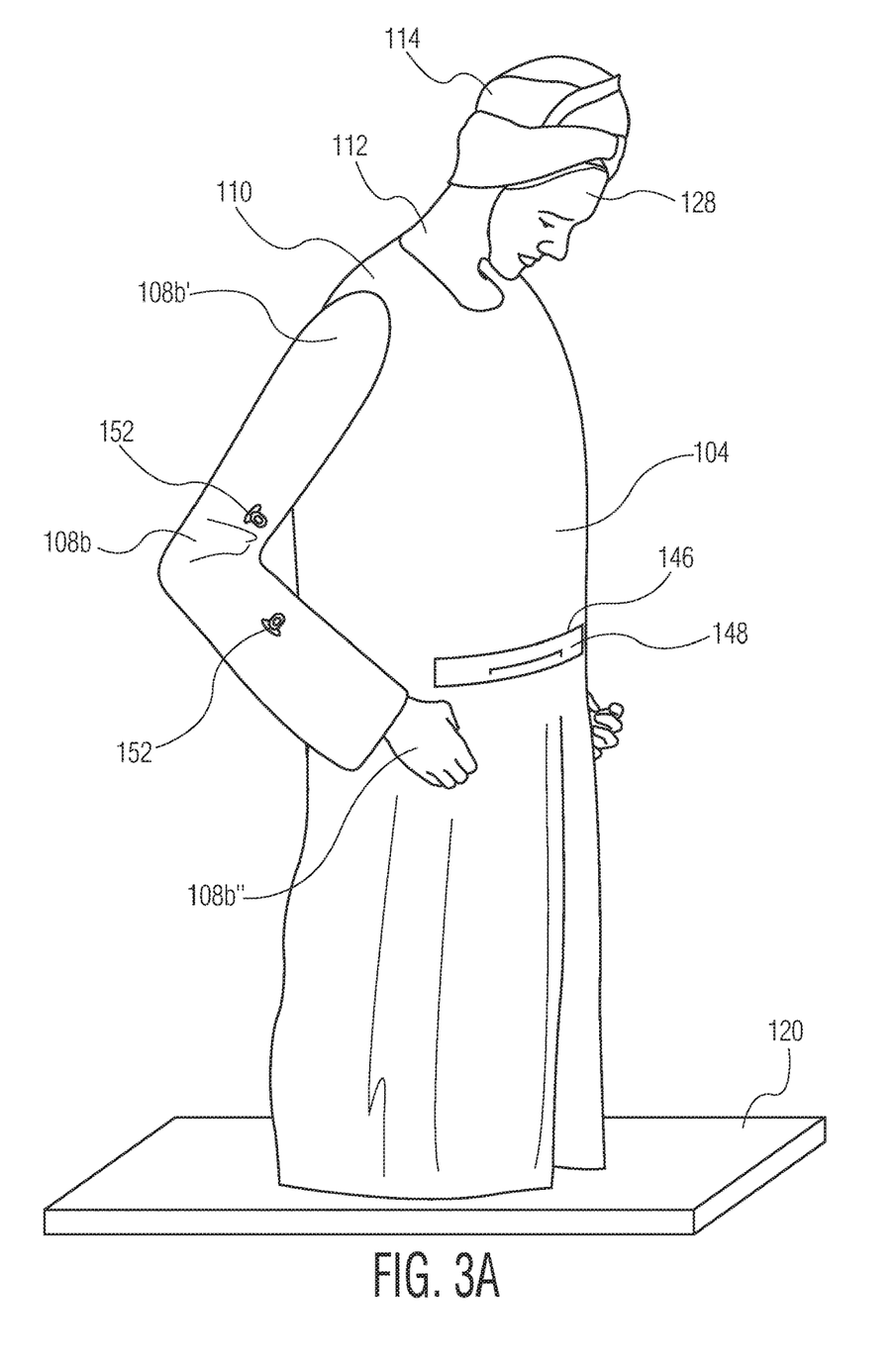
FIG. 3A is a side perspective view of an exemplary infant swing according to other embodiments of the present invention.
Figure 3B:
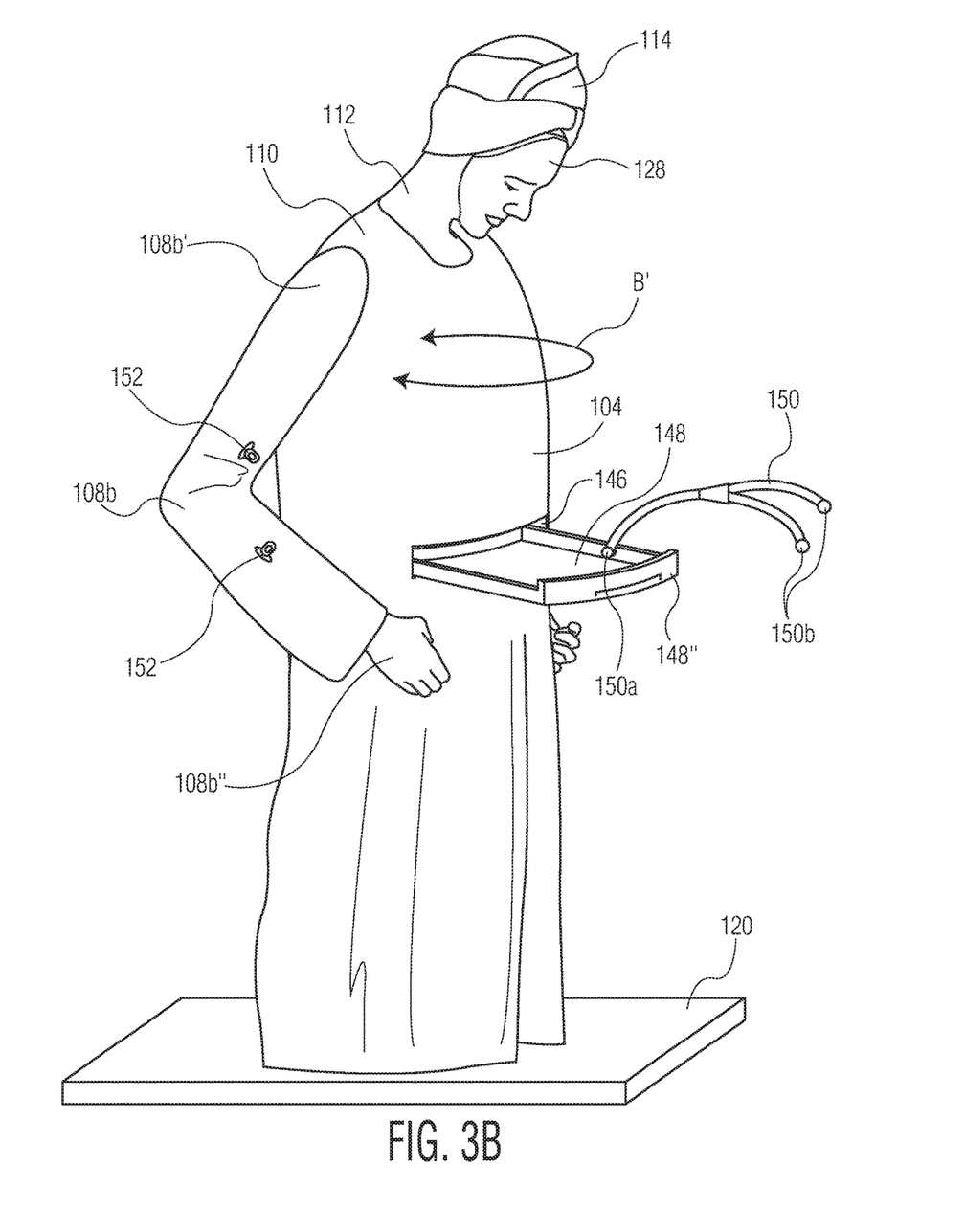
FIG. 3B is a side perspective view of the exemplary infant swing of FIG. 3A according to other embodiments of the present invention.

In another embodiment, the anterior wall 138 of the mannequin torso of the mannequin infant swing 100 defines one or more slots 146 configured to receive a shelf bed 148, which is moveable from a stored position within the torso 104, as illustrated in FIG. 3A, to an infant supporting position extended outwardly from the anterior surface 138 of the torso 104, as illustrated in FIG. 3B. Preferably, the mannequin infant swing 100 further comprises two or more arms 108 operatively connected to the upper chest portion 104a of the mannequin torso 104, wherein an anterior surface 138 of the mannequin torso 104 defines one or more slots 146 configured to receive a shelf bed 148, and the shelf bed 148 is moveable from a stored position within the mannequin torso 104 to an infant supporting position extended outwardly from the anterior surface 138 of the torso 104, and the arms 108a, 108b are configured to support the infant shelf bed 148 when the shelf bed 148 is in the infant supporting position, as illustrated in FIG. 3C and FIG. 4.

In embodiments of the invention, the mannequin infant swing 100 comprises a mannequin torso 104 having a form simulating a human or an animal.

Referring to FIGS. 3A-5, in a preferred embodiment of the present invention, an infant swing 100 is provided comprising an animated body 104 simulating a human form having a hollow torso 104 defining one or more slots 146 across its frontal plane, wherein such slots 146 are adapted to receive an infant shelf bed 148, preferably having a planar body, extending into the torso 104. The shelf bed 148 is moveable between a stored position disposed substantially within the torso as seen in FIG. 3A and an infant support position protruding outwardly from the torso 104 as seen in FIG. 3B. The torso 104 preferably has at least two opposing arms 108a, 108b, and each arm 108a, 108b has a proximal end 108a', 108b' pivotally connected to said torso 104 and a distal end 108a", 108b".

Figure 3C:
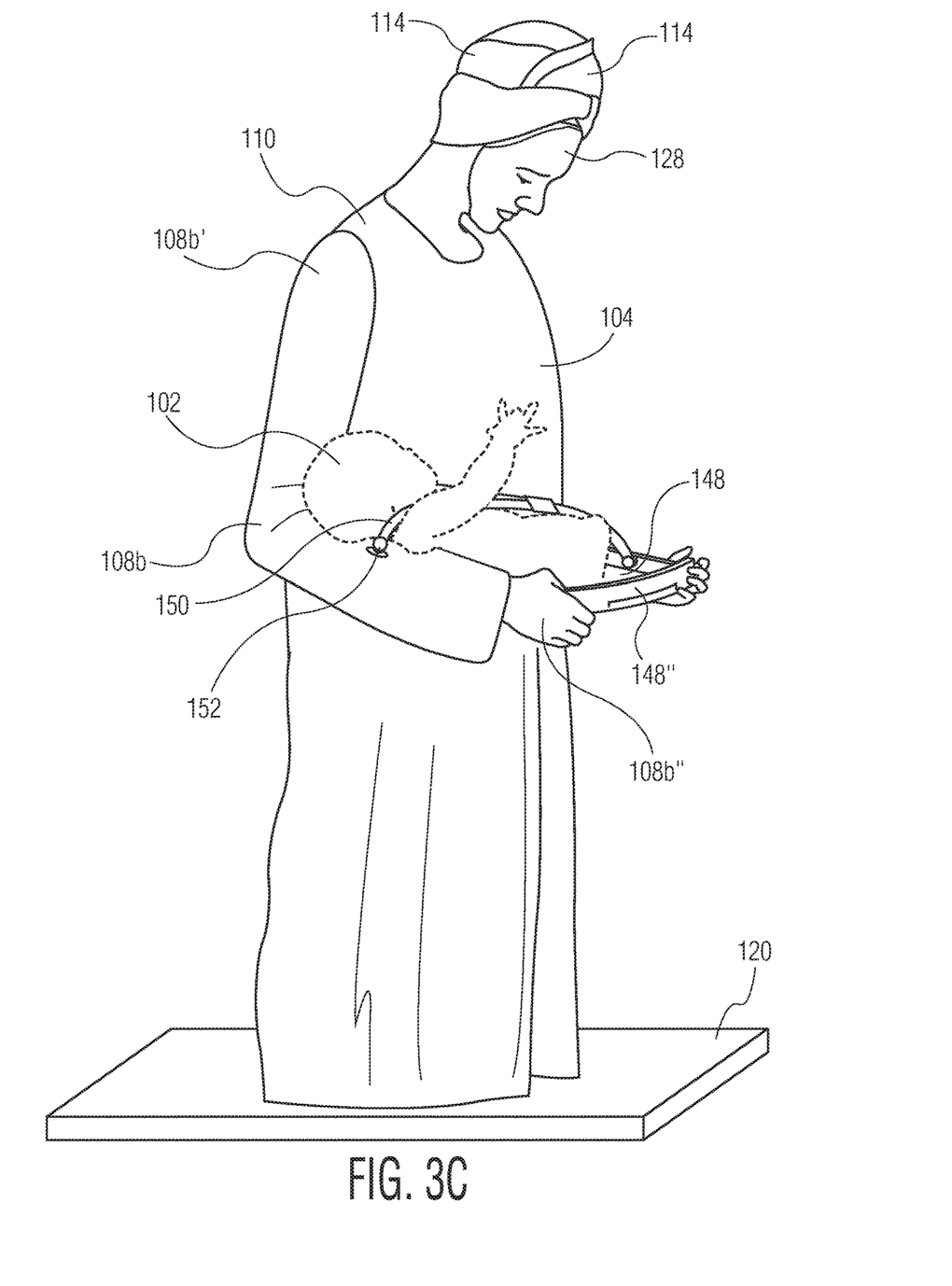
FIG. 3C is a side perspective view of the exemplary infant swing of FIG. 3A and FIG. 3B according to other embodiments of the present invention.
Figure 4:
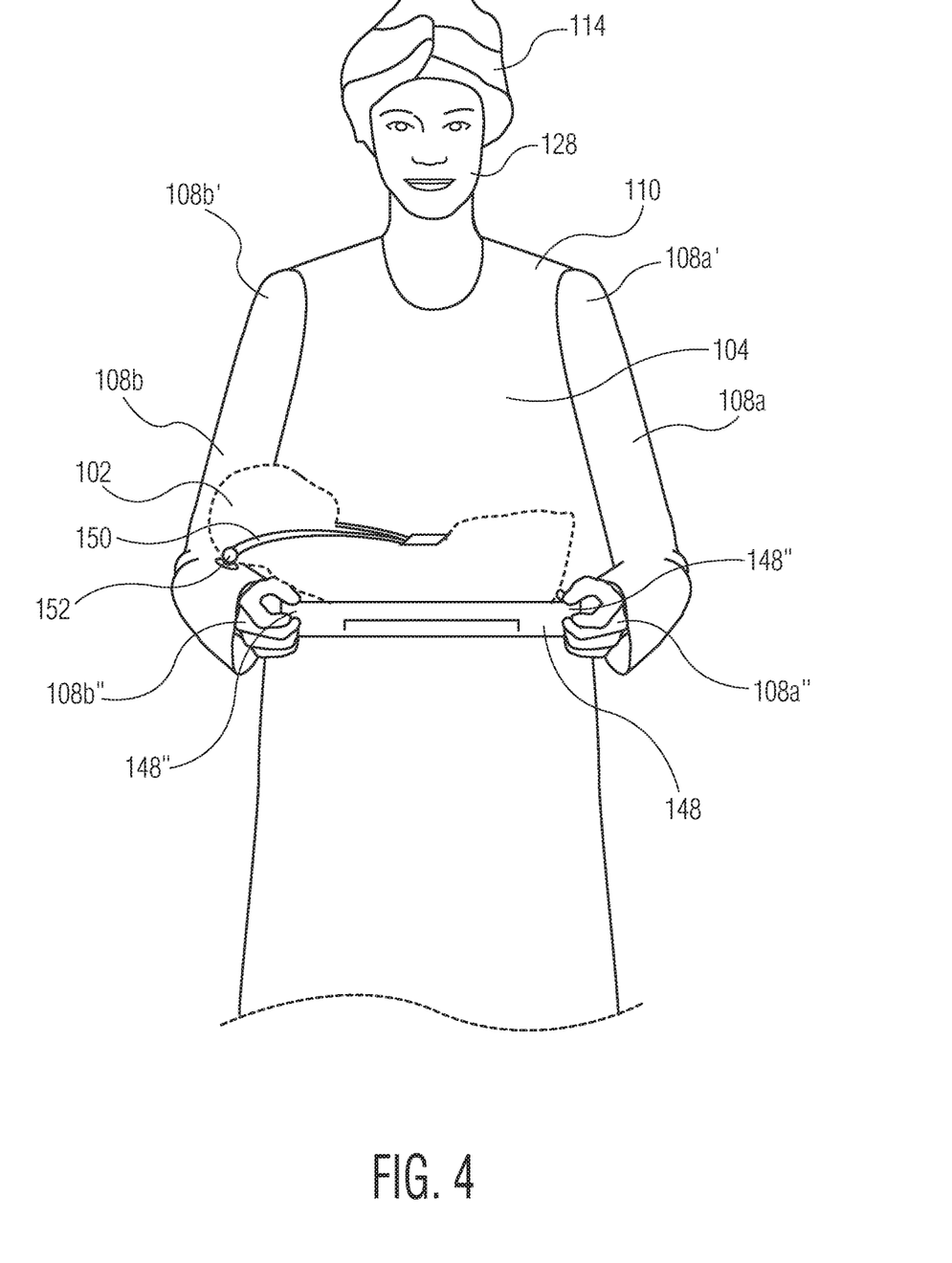
FIG. 4 is a front elevation view of embodiments illustrated in FIG. 3C.

The distal end 108a", 108b" of each respective arm 108 is preferably configured to rotate about the proximal end 108a', 108b' and is adapted to engage a distal end 148" of the infant shelf bed 148 to support the distal shelf end 148" against gravitational and centrifugal forces when the infant shelf bed 148 is in the infant support position, as exemplified in FIG. 3C and FIG. 4.

As seen in FIGS. 3B, 3C and 4, the infant swing preferably comprises a safety strap 150 having a first end 150a connected to one side of the shelf bed 148 and having at least a second end 150b removably connected to one of the arms 108a, 108b, of the mannequin body 104. One of such arms 108a, 108b preferably comprises one or more receiving connectors 152 disposed on an outer surface of the arm 108, such that the second end 150b of the safety strap 150 can be connected to the arm 108, to provide a safe and secure holding and swinging of the infant, when the arm 108 is supporting the shelf bed 148 in the infant supporting position.

In such embodiment, the infant swing 100 further comprises a motor 121 for driving the body 104 to pivot in a reciprocating motion relative to the base 120, and thus, causing the infant shelf bed 148 to swing along a horizontal arc B' as seen in FIG. 3B. The infant swing 100 further comprises a vertical support shaft 122 having a top end connected to the animated body 104 and a bottom end connected to and rotatable by the motor 121.

In such embodiment, the infant swing 100 further comprises a head portion 114 operatively connected atop the animated body 104 and configured to receive a mask 128 simulating a human face, and a simulated face mask 128 is operatively coupled to the head portion 114. In such embodiment, a sound recorder and converter 130 is disposed within the head portion 114 for playing sounds for the infant, at the option of a user.

In one embodiment, the torso 104 defines at least two slots 148, such that each of the slots 148 is configured on a diagonal relative to the horizontal plane.

In yet another embodiment, the shaft 122 of the infant swing 100 is hollow and thus provides a passageway for the communication of electrical wires 124 to extend therethrough from the base 120 through the torso 104.

The face mask 128 of the infant swing 100 is preferably a constructed from materials selected from a group consisting of resin, rubber, plastic, plaster, and plaster-like composition. The face mask 128 of the infant swing 100 is preferably constructed of a hard resin composite in full 24-bit color. In yet another embodiment, the face mask 128 of the infant swing 100 is constructed of laminated paper, configured to peal and stick onto the head portion 114. In such embodiment, an image of a person's face is printed onto the laminated paper face mask 128, wherein a first portion of the laminated paper is peeled away from an opposing second portion of the laminated paper thereby exposing an adhesive laminated surface of the second portion which is configured to stick to the head portion 114 of the infant swing 100. In such embodiment, the laminated paper face mask 128 is preferably connects to the front of the head portion 114 of the infant swing 100, as illustrated by arrow C in FIG. 5.

As illustrated in FIG. 2, the infant swing 100 preferably comprises clothing 154 adapted to be worn by the mannequin torso 104 of the infant swing 100, which simulates a human caretaker, such as for instance, preferably a nightgown 154 fitted around and worn by the infant swing 100. The infant swing 100 preferably comprises a turban 156 fitted atop an upper portion of the head portion 114, as seen in FIG. 2.

It should be appreciated from the above example embodiments and explanations that the compact portable infant swing 100 is preferably configured to be easily and quickly moved to multiple locations without requiring much assembly; and when stored it may be stood upright freestanding on its own due to its base and vertically extending leg 122; and it does not require significant storage space.

It should also be appreciated from the above that the infant swing 100 of the present disclosure more closely resembles the human body of a caretaker as compared to conventional infant swings, to enable the infant swing to be more comforting and soothing to an infant, while lessening the body fatigue of a caretaker tending to the infant.

The claimed invention is:

1. An infant swing comprising:
an animated body comprising a flexible hollow casing simulating a human form, said body including:
an upper body portion forming a simulated human trunk, arms, shoulders, neck and head portions, and a lower body portion;
said arms being sized and configured to firmly and removably engage and secure a portion of an outer surface of a body of the infant;
a frontally worn infant carrier of flexible fabric configured to receive an infant having shoulder straps removably connected to the shoulders such that reciprocating motion of the animated body imparts swinging motion to the infant carrier along a horizontal arc relative to a vertical axis of the animated body; each shoulder comprising a hook extending therefrom, such that the shoulder straps of the frontally worn infant carrier are configured to hook thereupon;
a base comprising a motor having a vertically extending shaft operatively connected to the lower body portion for pivoting said animated body in a reciprocating motion relative to said base, and thus, swinging the infant relative to said animated body for comforting the infant.

2. The infant swing of claim 1, wherein said head portion comprises an interchangeable simulated human face portion resemblant of a face of a user adapted to comfort the infant.

3. The infant swing of claim 1, wherein said head portion comprises an interchangeable simulated animal face portion resemblant of a face of an animal configured to comfort the infant.

4. The infant swing of claim 1, further comprising a voice recorder disposed within said animated body, said voice recorder electronically connected to a power source and adapted to record a voice from a user to form a voice message, and a sound converter disposed within said animated body, said sound converter electrically connected with said voice recorder for converting said voice message in an audible form.

5. The infant swing of claim 1, further comprising a sound recorder disposed within said animated body, said sound recorder electronically connected to a power source and adapted to record a heartbeat sound, and a sound converter disposed within said animated body, said sound converter electrically connected with said sound recorder for converting said heartbeat sound in an audible form.

6. The infant swing of claim 1, further comprising a sound recorder disposed within said animated body, said sound recorder electronically connected to a power source and adapted to record a womb sound, and a sound converter disposed within said animated body, said sound converter electrically connected with said sound recorder for converting said womb sound in an audible form.

7. The infant swing of claim 1, further comprising a sound recorder disposed within said animated body, said sound recorder electronically connected to a power source and adapted to store music, and a sound converter disposed within said animated body, said sound converter electrically connected with said sound recorder for converting said stored music in an audible form.

8. The infant swing of claim 1, wherein at least one arm comprises a vibrating motor embedded within said arm for soothing the infant when said arm secures the portion of the outer surface of the body of the infant.

9. The infant swing of claim 1, wherein the simulated human trunk comprises at least one vibrating motor embedded within said simulated human trunk for soothing the infant when positioned within the frontally worn infant carrier.

10. The infant swing of claim 1, wherein the lower body portion defines a cavity adapted for storage of the infant carrier within said cavity.

11. A mannequin infant swing comprising:
a mannequin torso having an upper chest portion and a lower abdominal portion, wherein an anterior surface of said mannequin torso defines one or more slots configured to receive a shelf bed, moveable from a stored position within said torso to an infant supporting position extended outwardly from the anterior surface of said torso;
an infant carrier comprising straps operatively worn by the mannequin torso, said infant carrier comprising flexible fabric configured to receive and securely hold an infant;
a head portion operatively connected to the mannequin torso by a neck portion,
a base having a motor including a vertical motor shaft configured to pivotally oscillate said vertical shaft relative to the base, said vertical shaft connected to said lower abdominal portion such that, in operation, pivoting of the vertical shaft imparts swinging of said infant carrier relative to said mannequin torso.

12. The mannequin infant swing of claim 11, wherein said head portion is configured to receive a simulated human face mask.

13. The mannequin infant swing of claim 11, wherein said head portion is configured to receive a simulated animal face mask.

14. The mannequin infant swing of claim 11, further comprising a simulated human face mask operatively connected to said head portion and configured to reflect a face of a caretaker.

15. The mannequin infant swing of claim 11, further comprising a simulated human face mask configured to reflect a face of a caretaker, wherein said simulated face mask is a 3D-printed face mask.

16. The mannequin infant swing of claim 11, further comprising a simulated animal face mask configured to reflect a face of an animal.

17. The mannequin infant swing of claim 11, further comprising a face mask, wherein said face mask is a 3D-printed face mask.

18. The mannequin infant swing of claim 11, further comprising a voice recorder disposed within said head portion, said voice recorder electronically connected to a power source and adapted to record a voice from a user to form a voice message, and a sound converter disposed within said head portion, said sound converter electrically connected with said voice recorder for converting said voice message in an audible form.

19. The mannequin infant swing of claim 11, further comprising a sound recorder disposed within said mannequin torso, said sound recorder electronically connected to a power source and adapted to record a heartbeat sound, and a sound converter disposed within said mannequin torso, said sound converter electrically connected with said sound recorder for converting said heartbeat sound in an audible form.

20. The mannequin infant swing of claim 11, an anterior surface of the lower abdominal portion having a hinged lid providing access to a cavity defined by said lower abdominal portion adapted for storage of the infant carrier within said cavity.

21. The mannequin infant swing of claim 11, wherein the straps comprise a set of shoulder straps and a set of side straps configured to extend around the mannequin torso.

22. The mannequin infant swing of claim 11, further comprising one or more arms operatively connected to said mannequin torso, wherein at least one arm comprises a vibrating motor disposed therein electrically connected to a power source.

23. The mannequin infant swing of claim 11, wherein the upper chest portion comprises an anterior wall having a heating pad electrically connected to a power source.

24. The mannequin infant swing of claim 11, wherein the upper chest portion comprises an anterior wall having a vibrating motor electrically connected to a power source.

25. The mannequin infant swing of claim 11, further comprising a shelf bed operatively coupled to the mannequin torso.

26. The mannequin infant swing of claim 11, further comprising two or more arms operatively connected to the upper chest portion of the mannequin torso, said arms configured to support the infant shelf bed when in said infant supporting position.

27. The mannequin infant swing of claim 11, wherein the mannequin torso comprises a form simulating a human or animal.

28. The mannequin infant swing of claim 11, further comprising clothing adapted to be worn by the mannequin torso.

29. The mannequin infant swing of claim 11, further comprising a turban adapted to be worn by the head portion.

30. An infant swing comprising:
an animated body simulating a human form having a hollow torso defining one or more slots across its frontal plane adapted to receive an infant shelf bed extending into said torso, the shelf bed being moveable between a stored position disposed substantially within the torso and an infant support position protruding out from said torso, said torso comprising at least two arms, each arm having a proximal end pivotally connected to said torso and a distal end rotatable about said proximal end adapted to engage a distal end of the infant shelf bed to support said distal shelf end against gravitational and centrifugal forces when said infant shelf bed is in the infant support position;
a base comprising a motor for driving said body to pivot in a reciprocating motion relative to said base, and thus, said infant shelf bed to swing along a horizontal arc;
a vertical support shaft having a top end connected to said animated body and a bottom end connected to and rotatable by said motor;
a head portion operatively connected atop the animated body and configured to receive a mask simulating a human face;
a simulated face mask operatively coupled to said head portion; and
a sound recorder and converter disposed within said head portion for playing sounds at the option of a user.

31. The infant swing of claim 30, wherein the torso defines at least two slots, each of said slots configured on a diagonal relative to the horizontal plane.

32. The infant swing of claim 30, wherein said support shaft is hollow providing a passageway for the communication of electrical wires to extend therethrough from said base through said torso.

33. The infant swing of claim 30, further comprising a shelf bed having straps connected to said shelf bed and adapted to securely retain an infant.

* * * * *